United States Patent [19]

Hansenne et al.

[11] Patent Number: 5,618,520
[45] Date of Patent: Apr. 8, 1997

[54] PHOTOSTABLE FILTERING COSMETIC COMPOSITION CONTAINING A UV-A FILTER AND A FILTERING POLYMER OF THE BENZOTRIAZOLE SILCONE TYPE

[75] Inventors: Isabelle Hansenne, Paris; Serge Forestier, Claye-Souilly; Andre Deflandre, Orry la Ville, all of France

[73] Assignee: L'Oreal, Paris, France

[21] Appl. No.: 382,310

[22] PCT Filed: Sep. 15, 1993

[86] PCT No.: PCT/FR93/00886

§ 371 Date: May 4, 1995

§ 102(e) Date: May 4, 1995

[87] PCT Pub. No.: WO94/06404

PCT Pub. Date: Mar. 31, 1994

[30] Foreign Application Priority Data

Sep. 17, 1992 [FR] France .................... 92 11099

[51] Int. Cl.$^6$ .............. A61K 7/42; C08G 77/00; C07C 49/82
[52] U.S. Cl. .............. 424/59; 424/63; 424/70.1; 514/938; 528/12; 568/331
[58] Field of Search ............. 424/59, 63, 70.1; 568/331; 514/938

[56] References Cited

U.S. PATENT DOCUMENTS 4,387,089  7/1983  De Polo ................... 424/59

5,089,250  2/1992  Forestier et al. ............. 424/43

FOREIGN PATENT DOCUMENTS 0365370  4/1990  European Pat. Off. .
0392883  10/1990  European Pat. Off. .
2440933  6/1980  France .
2680683  5/1993  France .

Primary Examiner—Shelley A. Dodson
Attorney, Agent, or Firm—Jacobson, Price, Holman & Stern, PLLC

[57] ABSTRACT

A photostable, filtering cosmetic composition for protecting human epidermis and hair against UV rays comprises, in a cosmetically acceptable carrier having at least one fatty phase 0.5 to 4% by weight of 4-(tert.-butyl) 4'-methoxy dibenzoylmethane and 0.1 to 20% by weight of a filtering polymer of the benzotriazole silicone type containing at least one unit of formula (1), where R' is a $C_1$-$C_{30}$ hydrocarbon group, a $C_1$-$C_8$ halogenated hydrocarbon group or a trimethylsilyloxy group; a is 1 or 2; X=—A—Y where A is an aliphatic or aromatic bivalent hydrocarbon radical having at least 2 carbon atoms and optionally containing one or more oxygen atoms; Y is a 2-(2'-hydroxyphenyl)benzotriazole residue optionally containing one or more $C_1$-$C_8$ alkyl, $C_2$-$C_8$ alkenyl, halogen, alkoxy, carboxy, hydroxy or amino substituents, the weight ratio of the benzotriazole silicone to the 4-(tert.-butyl) 4'-methoxy dibenzoylmethane being between 1 and 10.

13 Claims, No Drawings

PHOTOSTABLE FILTERING COSMETIC COMPOSITION CONTAINING A UV-A FILTER AND A FILTERING POLYMER OF THE BENZOTRIAZOLE SILCONE TYPE

The present invention relates to a photostable cosmetic composition intended to protect the skin and the hair from UV radiation, containing a UV-A filter and a filtering polymer of the benzotriazole silicone type, to its use for protection of the skin and the hair against UV rays and to a process for the stabilization of the UV-A filter by a benzotriazole silicone.

It is known that light radiation with wavelengths between 280 nm and 400 nm permit tanning of the human epidermis and that rays with wavelengths between 280 and 320 nm, which are known under the name UV-B, cause erythema and skin burns which may be harmful to the development of the tan; this UV-B radiation should thus be filtered out.

It is also known that UV-A rays, with wavelengths between 320 and 400 nm, which cause tanning of the skin, are liable to induce damage of the latter especially in the case of sensitive skin or skin which is continually exposed to solar radiation. UV-A rays in particular cause a loss in elasticity of the skin and the appearance of wrinkles, leading to premature ageing. They promote the triggering of the erythemal reaction or amplify this reaction in certain individuals and may even be the cause of phototoxic or photoallergic reactions. It is thus desirable also to filter out the UV-A radiation.

French Patent No. 2,440,933 describes 4-(tert-butyl)-4'-methoxydibenzoylmethane as a UV-A filter. It is proposed to combine this specific UV-A filter, sold under the name "PARSOL 1789" by the company Givaudan, with various UV-B filters for the purpose of absorbing all of the UV rays with wavelengths between 280 and 380 nm.

Unfortunately, when this UV-A filter is used alone or in combination with UV-B filters, it does not possess a photochemical stability which is satisfactory to guarantee constant protection of the skin during prolonged exposure to the sun, thereby necessitating repeated applications at close and regular intervals if it is desired to obtain effective protection of the skin against UV rays.

The Applicant has discovered that by combining, in defined proportions and in a defined weight ratio, 4-(tert-butyl)-4'-methoxydibenzoylmethane with a filtering polymer of the benzotriazole silicone type containing at least one unit of formula:

   (I)

in which

R' denotes a saturated or unsaturated $C_1$–$C_{30}$ hydrocarbon group, a $C_1$–$C_8$ halogenated hydrocarbon group or a trimethylsilyloxy group;

a=1 or 2;

X=—A—Y where A represents an aliphatic or aromatic divalent hydrocarbon radical containing at least 2 carbon atoms and optionally containing one or more oxygen atoms;

Y represents a 2-(2'-hydroxyphenyl)benzotriazole residue optionally bearing, on one or both of the aromatic rings, one or more $C_1$–$C_8$ alkyl, $C_2$–$C_8$ alkenyl, halogen, alkoxy, carboxyl, hydroxyl or amino substituents, satisfactory photochemical stability of the 4-(tert-butyl)-4'-methoxydibenzoylmethane was, surprisingly, obtained. A stabilized combination for protecting the human epidermis and hair against UV rays with wavelengths between 280 and 380 nm is thus available.

Furthermore, such a combination imparts to the filtering composition containing it, besides a good UV-A protection number and a good sun protection factor, enhanced cosmetic properties as regards the sticky effect on application and the final greasy appearance after penetration, as well as lasting properties in water, that is to say a good stability of the protection number over time, especially after showering or bathing.

The UV-A protection number and the sun protection factor (SPF) are determined using the in vitro method described by B. L. Diffey et al., in J. Soc. Cosmet. Chem. 40-127–133 (1989).

This method consists in determining the monochromatic protection factors every 5 nm over a wavelength range from 290 to 400 nm and in calculating, from these protection factors, the solar protection factor.

In addition to the units of formula (I), the filtering polymer may contain units of formula:

   (II)

in which R' has the same meaning as in formula (I);

b is an integer denoting 1, 2 or 3.

Hydrocarbon groups which may be mentioned are $C_1$–$C_{30}$ alkyl radicals, $C_2$–$C_{30}$ alkenyl radicals, cycloalkyl radicals or aromatic radicals such as phenyl or tolyl.

A halogenated hydrocarbon group which may be mentioned is the 3,3,3-trifluoropropyl radical.

In the filtering polymer consisting of moieties (I) and optionally (II), at least 40% in numerical terms of the radicals R' are methyl radicals. The total number of the units (I) and (II) is preferably less than or equal to 250 and is in particular between 2 and 50.

Such siloxane-chain filtering polymers are described in particular in European Patent Application Nos. 0,388,218 and 0,392,883.

On account of their lipophilic nature, the filters used are distributed uniformly in the conventional cosmetic vehicles containing at least one fatty phase or take the form of aqueous dispersions of lipid vesicles and may thus be applied to the skin in order to form an effective protective film.

The subject of the present invention is thus a photostable cosmetic composition which protects the skin or the hair against UV radiation with wavelengths between 280 and 380 nm and which comprises, in a cosmetically acceptable vehicle containing at least one fatty phase, 0.5 to 4% by weight of 4-(tert-butyl)-4'-methoxydibenzoylmethane and 0.1 to 20% by weight, preferably 0.5 to 15%, of benzotriazole silicone as defined above, the weight ratio of the benzotriazole silicone to the 4-(tert-butyl)-4'-methoxydibenzoylmethane being between 1 and 10.

The upper limit of this ratio is determined by the solubility of the filters in the fatty phase used in the composition or in the lipid phase present in the vesicle dispersion.

Another subject of the present invention is a cosmetic treatment process for the skin or the hair which is intended to protect them against the effects of UV rays with wavelengths between 280 and 380 nm, which consists in applying to the latter an effective amount of a cosmetic composition as defined above.

Another subject of the present invention consists of a process for the stabilization of 4-(tert-butyl)-4'-methoxydibenzoylmethane with regard to UV radiation using a benzotriazole silicone as defined above, in which process 0.1 to 20% by weight of benzotriazole silicone defined above is used in order to stabilize from 0.5 to 4% by weight of 4-(tert-butyl)-4'-methoxydibenzoylmethane, the weight ratio of the benzotriazole silicone to the 4-(tert-butyl)-4'-methoxydibenzoylmethane being between 1 and 10.

The cosmetic composition of the invention may be used as a composition for protecting the human epidermis or the hair against ultraviolet rays, as an antisun composition or as a make-up product.

This composition may in particular be in the form of a lotion, a thickened lotion, a gel, an oil, a vesicle dispersion, an emulsion such as a cream or milk, a powder or a solid stick, and may optionally be packaged as an aerosol and be in the form of a foam or spray.

It may contain the cosmetic adjuvants usually used such as fats, organic solvents, silicones, thickeners, softeners, anti-foaming agents, hydrating agents, fragrances, preserving agents, anionic, cationic, nonionic or amphoteric surfactants or mixtures thereof, fillers, sequestering agents, anionic, cationic, nonionic or amphoteric polymers or mixtures thereof, propellants, basifying or acidifying agents, dyes, metal oxide pigments of particle size between 100 nm and 20,000 nm such as iron oxides, or any other ingredient usually used in cosmetics.

The fats may consist of an oil or a wax or a mixture thereof, fatty acids, fatty acid esters, fatty alcohols, petrolatum, paraffin, lanolin, hydrogenated lanolin or acetylated lanolin.

The oils are chosen from animal, plant, mineral and synthetic oils and especially hydrogenated palm oil, hydrogenated castor oil, liquid petrolatum, paraffin oil, purcellin oil, silicone oils and isoparaffins.

The waxes are chosen from animal, fossil, plant, mineral and synthetic waxes. Bees waxes, carnauba wax, candelila wax, sugar cane wax, Japan wax, ozokerites, montan wax, microcrystalline waxes, paraffins, and silicone resins and waxes may be mentioned in particular.

The composition according to the invention may also contain metal oxide nanopigments dispersed in the fatty phase and/or in the aqueous phase.

It may also contain other lipophilic UV filters and especially UV-B filters.

The composition according to the invention may be in the form of a vesicle dispersion of amphiphilic ionic or nonionic lipids, which is prepared according to known processes. It is possible, for example, to swell the lipids in an aqueous solution in order to form spherules which are dispersed in the aqueous medium, as described in the article Bangham, Standish & Watkins, J. mol. Biol., 13, 238 (1965) or in Patents FR-2,315,991 and 2,416,008 from the Applicant. The description of the various modes of preparation will be found in "Les liposomes en biologie cellulaire et pharmacologie" [Liposomes in cellular biology and pharmacology], edition INSERM/John Libbery Eurotext, 1987, pages 6 to 18.

When the composition is in the form of an emulsion or a vesicle dispersion, the aqueous phase may contain water-soluble UV filters such as benzene-1,4-[di(3-methylidene-10-camphorsulfonic)] acid, 2-phenylbenzimidazole-5-sulfonic acid or 2-hydroxy-4-methoxybenzophenone-5-sulfonic acid, these acids being or not being salified.

In the case of a composition packaged as an aerosol, conventional propellants such as alkanes, fluoroalkanes and chlorofluoroalkanes are used.

When the cosmetic composition according to the invention is used for the protection of the human epidermis against UV rays, or as an antisun composition, it may be in the form of a suspension or a dispersion in solvents or fats, in the form of a vesicle dispersion or an oil, or alternatively in the form of an emulsion such as a cream or milk, or in the form of an ointment, a gel, a solid stick or an aerosol foam.

When the cosmetic composition according to the invention is used for the protection of the hair, it may be in the form of a shampoo, a lotion, a gel, an emulsion, a vesicle dispersion or a lacquer for the hair and may consist, for example, of a composition to be rinsed, to be applied before or after shampooing, before or after dyeing or bleaching, or before, during or after permanent-waving or straightening of the hair, a styling or treating lotion or gel, a lotion or gel for blow drying or hairsetting, or a composition for the permanent-waving, straightening, dyeing or bleaching of the hair.

When the composition is used as a make-up product for the eyelashes, the eyebrows or the skin, such as a treatment cream for the epidermis, a foundation, a lipstick, an eyeshadow, a blusher, a mascara or an eyeliner, it may be in solid or pasty, anhydrous or aqueous form, such as oil-in-water or water-in-oil emulsions, vesicle dispersions or alternatively suspensions.

The invention will be better illustrated by the non-limiting examples below.

EXAMPLE 1

An oil-in-water antisun emulsion having the following composition is prepared:

| | |
|---|---|
| 4-tert-Butyl-4'-methoxydibenzoylmethane | 2 g |
| Polydimethylsiloxane containing 2-(3'-trimethylene-2'-hydroxy-5'-methylphenyl)benzotriazole grafts corresponding to the Patent Application EP 0 392,883, of formula | 6 g |

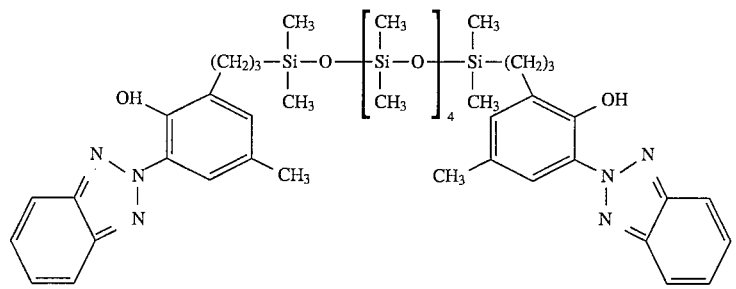

| | |
|---|---|
| Mixture of cetyl/stearyl alcohol and oxyethylenated cetyl/ | 7 g |

| | | |
|---|---|---|
| stearyl alcohol containing 33 mol of ethylene oxide, sold under the name "SINNOWAX AO" by the company Henkel | | |
| Mixture of non-autoemulsifiable glycol mono- and distearate | | 2 g |
| Cetyl alcohol | | 1.5 g |
| Polydimethylsiloxane sold under the name DC 200-350 CST by the company Dow Corning | | 1.5 g |
| Capric and caprylic acid triglycerides sold under the name MIGLYOL 812 by the company Huls | | 15 g |
| Glycerol | | 20 g |
| Preserving agents | qs | |
| Sequestering agent | | 0.1 g |
| Water | qs | 100 g |

EXAMPLE 2

An antisun oil of the following composition is prepared:

| | |
|---|---|
| 4-tert-Butyl-4'-methoxydibenzoylmethane | 3 g |
| Polydimethylsiloxane containing the 2-(3'-trimethylene-2'-hydroxy-5'-methylphenyl) benzotriazole graft of Example 1 of Application EP-A-0,392,883, of formula: | 8 g |

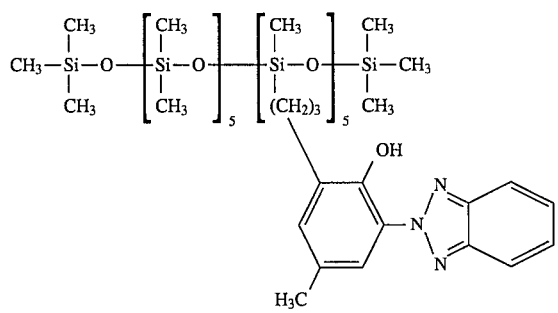

| | | |
|---|---|---|
| Titanium oxide nanopigment sold under the name TiO$_2$ MOTG by the company Tioxide | | 5 g AM |
| Diisopropyl adipate | qs | 100 g |

EXAMPLE 3

An antisun emulsion having the following composition is prepared:

| | |
|---|---|
| 4-tert-Butyl-4'-methoxydibenzoylmethane | 1 g |
| Polydimethylsiloxane containing the 2-(3'-trimethylene-2'-hydroxy-5'-methylphenyl) benzotriazole graft of Example 1 of Application EP-A-0,388,218, of formula: | 5 g |

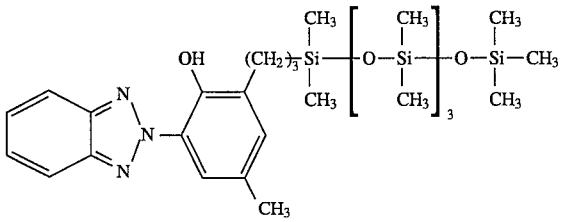

| | | |
|---|---|---|
| Sorbitan monostearate | | 5 g |
| Hydrophobic pyrogenous silica sold under the name AEROSIL R 972 by the company Degussa | | 0.5 g |
| Benzene-1,4-di(3-methylidene-10-camphor-sulfonic) acid | | 3 g |
| Triethanolamine | qs | pH7 |
| Benzoate of C$_{12}$–C$_{15}$ alcohols sold under the name "FINSOLV TN" by the company Witco | | 15 g |
| Purified water | qs | 100 g |

EXAMPLE 4

A day cream for the face having the following composition is prepared:

| | |
|---|---|
| 4-tert-Butyl-4'-methoxydibenzoylmethane | 1.5 g |
| Polydimethylsiloxane containing 2-(3'-trimethylene-2'-hydroxy-5'-methylphenyl)benzotriazole grafts according to the Patent Application EP 0 392,883, of formula | 1.5 g |

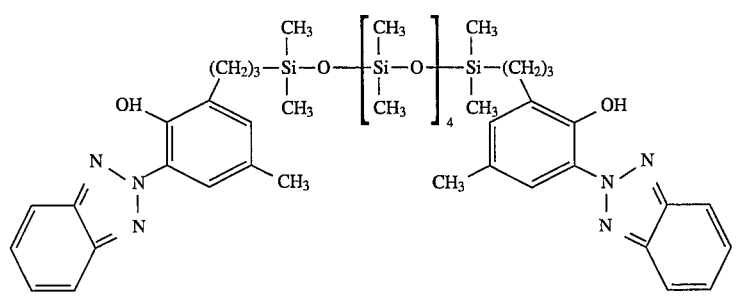

| | |
|---|---|
| Mixture of cetyl/stearyl alcohol and oxyethylenated cetyl/stearyl alcohol containing 33 mol of ethylene oxide, sold under the name "SINNOWAX AO" by the company Henkel | 7 g |
| Mixture of non-autoemulsifiable glycol mono- and distearate | 2 g |
| Cetyl alcohol | 1.5 g |

| | | |
|---|---|---|
| Polydimethylsiloxane, sold under the name DC 200-350 CST by the company Dow Corning | | 1.5 g |
| Capric and caprylic acid triglycerides sold under the name MIGLYOL 812 by the company Huls | | 15 g |
| Glycerol | | 20 g |
| Preserving agents | qs | |
| Sequestering agent | | 0.1 g |
| Water | qs | 100 g |

EXAMPLE 5

| | | |
|---|---|---|
| Hair-protecting lotion: | | |
| 4-tert-Butyl-4'-methoxydibenzoylmethane | | 0.5 g |
| Silicone containing 2-(3'-trimethylene-2'-hydroxy-5'-methylphenyl)benzotriazole grafts of formula (silicone B): | | 2 g |

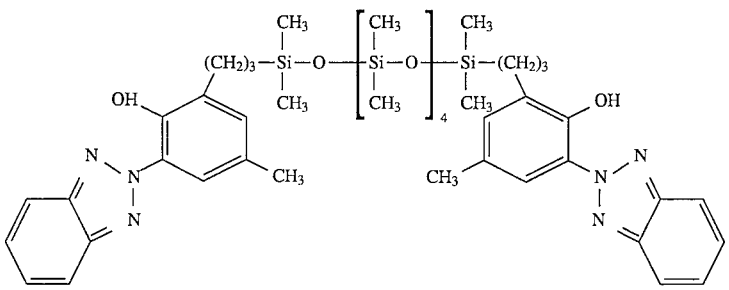

| | | |
|---|---|---|
| Benzoate of $C_{12}/C_{15}$ alcohols, sold under the name "FINSOLV TN" by the company Witco | | 12 g |
| Ethyl alcohol | qs | 100 g |

EXAMPLE 6

Oil-in-water antisun emulsion:

| | |
|---|---|
| 4-tert-Butyl-4'-methoxydibenzoylmethane | 1.75 g |
| Silicone containing a 2-[3'-(2''-methyltrimethylene)-2'-hydroxy-5'-methylphenyl]benzotriazole graft of formula (silicone C): | 5 g |

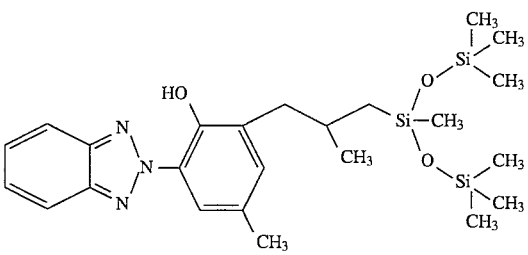

| | | |
|---|---|---|
| Mixture of cetyl/stearyl alcohol and oxyethylenated cetyl/stearyl alcohol containing 33 mol of ethylene oxide, sold under the name "SINNOWAX AO" by the company Henkel | | 8 g |
| Mixture of non-autoemulsifiable glyceryl mono- and distearate | | 2 g |
| Cetyl alcohol | | 2 g |
| Diisopropyl adipate | | 10 g |
| Liquid petrolatum | | 5 g |
| Glycerol | | 10 g |
| Preserving agents | qs | |
| Water | qs | 100 g |

EXAMPLE 7

Water-in-oil antisun emulsion:

| | |
|---|---|
| 4-tert-Butyl-4'-methoxydibenzoylmethane | 1 g |
| Silicone containing a 2-(3'-trimethylene-2'-hydroxy-5'-methylphenyl)benzotriazole graft of formula (silicone A): | 2 g |

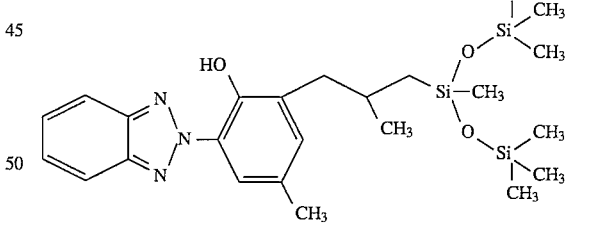

| | |
|---|---|
| Mixture (hydroxystearate and isostearate of sorbitol and of glycerol) oxypropylenated with 2 mol of propylene oxide and oxyethylenated with 3 mol of ethylene oxide, sold under the name "ARLACEL 780" by the company ICI | 6 g |
| Liquid petrolatum | 10 g |
| Capric and caprylic acid triglycerides sold under the name "MIGLYOL 812" by the company Huls | 5 g |
| beta-Hydroxyoctacosanyl 12-hydroxystearate sold under the name "ELFACOS C26" by the company AKZO | 3 g |
| Mixture of cyclopentadimethylsiloxane, cyclotetradimethylsiloxane and cyclohexadimethylsiloxane, sold under the name "DC 345 FLUID" by the company Dow Corning | 3 g |
| Glycerol | 5 g |

-continued

Water-in-oil antisun emulsion:

| | | |
|---|---|---|
| Magnesium sulfate | | 0.7 g |
| Preserving agents | qs | |
| Water | qs | 100 g |

Modes of Preparation of Silicones A, B and C

Silicone A

A mixture of 3-allyl-2-hydroxy-5-methylphenylbenzotriazole (5 g, 18 meq), bis(trimethylsiloxy)methylsilane (Petrarch Systems Inc., B 2497, 4.2 g, 18 meq as SiH) and cyclovinylmethylsiloxane complexed with platinum (Petrarch, PC085, 5 μl) in dry toluene (8 ml) at 60°–70° C. is heated to 40° C., with stirring and under nitrogen. The mixture is left stirring at 40° C. until the SiH groups have disappeared (absence of a peak at 2180 cm$^{-1}$ in infrared), which is equivalent to 2 hours. The solvent is evaporated off. The brown oil obtained is chromatographed on a column of silica (150 g, eluent: heptane/dichloromethane 80/20). After removal of the head fractions, the expected product is obtained in the form of a white powder (6 g, yield=65%).

$^{13}$C NMR Spectrum (CDCl$_3$): spectrum in accordance with the formula.

$^{29}$Si NMR Spectrum (CDCl$_3$): spectrum in accordance with the formula.

UV (Ethanol) $\lambda_{max}$=303 nm, $\epsilon_{max}$=16,000 $\lambda_{max}$=342 nm, $\epsilon_{max}$=15,300.

Analysis for C$_{23}$H$_{37}$N$_3$O$_3$Si$_3$

| | C | H | N | Si |
|---|---|---|---|---|
| Calculated | 56.63 | 7.65 | 8.61 | 17.27 |
| Found | 57.01 | 7.71 | 8.66 | 16.94 | m.p.=68° C.

Silicone B 1,1,3,3,5,5,7,7,9,9,11,11-Dodecamethylhexasiloxane (50 g, 232 meq as SiH) is added dropwise over one hour to a solution of 3-allyl-2-hydroxy-5-methylphenylbenzotriazole (61.6 g, 232 meq) and cyclovinylmethylsiloxane complexed with platinum (Petrarch PC085, 50 μl) in dry toluene (150 ml) at 80°–90° C., under nitrogen and with stirring. The mixture is left stirring at 80° C. until the SiH groups have disappeared (absence of a peak at 80 cm$^{-1}$ in infrared), which is equivalent to 4 hours. The solvent is evaporated off. The orange-colored viscous oil obtained (103 g) is purified on a column of silica (500 g, eluent heptane/dichloromethane 9/1 in order to remove the monomers and then heptane/dichloromethane/AcOH 90/9.8/0.2 to give the expected product in the form of a white wax (70 g, yield=63%).

$^{13}$C NMR Spectrum (CDCl$_3$): spectrum in accordance with the formula.

$^{29}$Si NMR Spectrum (CDCl$_3$): spectrum in accordance with the formula.

UV (Ethanol) $\lambda_{max}$=302 nm, $\epsilon_{max}$=30,200 $\lambda_{max}$=340 nm, $\epsilon_{max}$=27,700.

Analysis for C$_{44}$H$_{68}$N$_6$O$_7$Si$_6$

| | C | H | N | Si |
|---|---|---|---|---|
| Calculated | 54.96 | 7.13 | 8.74 | 17.52 |
| Found | 54.90 | 7.12 | 8.81 | 17.11 | m.p.=38° C.

Silicone C bis(Trimethylsiloxy)methylsilane (Petrarch Systems Inc., B 2497, 75.4 g, 322 meq as SiH) is added dropwise over 1 hour 15 minutes to a solution of 3-methallyl-2-hydroxy-5-methylphenylbenzotriazole (90 g, 322 meq) and cyclovinylmethylsiloxane complexed with platinum (Petrarch PC 085, 0.3 ml) in dry toluene (130 ml) at 80° C., under nitrogen and with stirring. The mixture is left stirring at 80° C. until the starting benzotriazole has disappeared, which is equivalent to 4 hours. The solvent is evaporated off. The brown oil obtained is crystallized from ethanol to give the expected product in the form of an off-white powder (97 g, yield=60%).

$^{13}$C NMR Spectrum (CDCl$_3$): spectrum in accordance with the formula.

$^{29}$Si NMR Spectrum (CDCl$_3$): spectrum in accordance with the formula.

UV (Ethanol) $\lambda_{max}$=303 nm, $\epsilon_{max}$=16,300 $\lambda_{max}$=343 nm, $\epsilon_{max}$=15,600.

Analysis for C$_{24}$H$_{39}$N$_3$O$_3$Si$_3$

| | C | H | N | Si |
|---|---|---|---|---|
| Calculated | 57.44 | 7.83 | 8.37 | 16.79 |
| Found | 57.35 | 7.76 | 8.09 | 16.51 | m.p.=49° C.

We claim:

1. Photostable filtering cosmetic composition for the protection of the skin and the hair against ultraviolet rays with wavelengths between 280 and 380 nm, comprising in a cosmetically acceptable vehicle containing at least one fatty phase, 0.5 to 4% by weight of 4-(tert-butyl)-4'-methoxydibenzoylmethane 0.1 to 20% by weight benzotriazole silicone of a filtering polymer containing at least one unit of formula:

in which

R' denotes a saturated or unsaturated C$_1$–C$_{30}$ hydrocarbon group, a C$_1$–C$_8$ halogenated hydrocarbon group or a trimethylsilyloxy group;

a=1 or 2;

X=—A—Y where A represents an aliphatic or aromatic divalent hydrocarbon radical containing at least 2 carbon atoms and optionally containing one or more oxygen atoms;

Y represents a 2-(2'-hydroxyphenyl)benzotriazole residue optionally bearing, on one or both of the aromatic rings, one or more C$_1$–C$_8$ alkyl, C$_2$–C$_8$ alkenyl, halogen, alkoxy, carboxyl, hydroxyl or amino substituents, the weight ratio of the benzotriazole silicone to the 4-(tert-butyl)-4'-methoxydibenzoylmethane being between 1 and 10.

2. Composition according to claim 1, wherein the benzotriazole silicone comprises, in addition to the units of formula (I), units of formula:

in which R' has the same meaning as in claim 1 and b is an integer denoting 1, 2 or 3, at least 40% of the radicals R' being methyl radicals.

3. Cosmetic composition according to claim 1, which is a composition for protecting the human epidermis or an antisun composition and is in the form of a lotion, a thickened lotion, a gel, an oil, a vesicle dispersion, a cream, a milk, a powder, a solid stick, a foam or a spray.

4. Cosmetic composition according to claim 1, which is a make-up composition for the eyelashes, the eyebrows or the skin and is in solid or pasty, anhydrous or aqueous form, in the form of an emulsion, a suspension or a vesicle dispersion.

5. Cosmetic composition according to claim 1, which is used for protection of the hair against ultraviolet rays, and is in the form of a shampoo, a lotion, a gel, an emulsion, a vesicle dispersion or a lacquer for the hair.

6. Composition according to claim 1, in the form of an emulsion or vesicle dispersion of ionic or nonionic amphiphilic lipids, and contains a water-soluble UV filter chosen from benzene-1,4-[di(3-methylidene-10-camphorsulfonic)] acid, 2-phenylbenzimidazole-5-sulfonic acid or 2-hydroxy-4-methoxybenzophenone-5-sulfonic acid, which may or may not be salified and which are present in the aqueous phase.

7. Cosmetic composition according to claim 1, which additionally comprises cosmetic adjuvants chosen from fats, organic solvents, silicones, thickeners, softeners, lipophilic UV-B sunscreen agents, anti-foaming agents, hydrating agents, fragrances, preserving agents, anionic, cationic, nonionic or amphoteric surfactants or mixtures thereof, fillers, sequestering agents, anionic, cationic, nonionic or amphoteric polymers or mixtures thereof, propellants, basifying or acidifying agents, dyes or metal oxide pigments of particle size between 100 nm and 20,000 nm.

8. Composition according to claim 1, which additionally contains metal oxide nanopigments dispersed in the fatty phase and/or in the aqueous phase.

9. Cosmetic treatment process for the skin and the hair for protecting them against the effects of UV rays with wavelengths between 280 and 380 nm, comprising applying to the skin or the hair an effective amount of a filtering cosmetic composition as defined in claim 1.

10. Process for the stabilization of 4-(tert-butyl)-4'-methoxydibenzoylmethane with regard to UV radiation, comprising adding 0.1 to 20% by weight, of a benzotriazole silicone filtering polymer containing at least one unit of formula:

in which

R' denotes a saturated or unsaturated $C_1$–$C_{30}$ hydrocarbon group, a $C_1$–$C_8$ halogenated hydrocarbon group or a trimethylsilyloxy group;

a=1 or 2;

X=—A—Y where A represents an aliphatic or aromatic divalent hydrocarbon radical containing at least 2 carbon atoms and optionally containing one or more oxygen atoms;

Y represents a 2-(2'-hydroxyphenyl)benzotriazole residue optionally bearing, on one or both of the aromatic rings, one or more $C_1$–$C_8$ alkyl, $C_2$–$C_8$ alkenyl, halogen, alkoxy, carboxyl, hydroxyl or amino substituents containing from 0.5 to 4% by weight of 4-(tert-butyl)-4'-methoxydibenzoylmethane; the weight ratio of the benzotriazole silicone to the 4-(tert-butyl)-4'-methoxydibenzoylmethane being between 1 and 10.

11. Process according to claim 10, wherein the benzotriazole silicone comprises, in addition to the units of formula (I), units of formula:

in which R' has the same meaning as in claim 10 and b is an integer denoting 1, 2 or 3, at least 40% of the radicals R' being methyl radicals.

12. Composition according to claim 1, wherein the composition contains 0.5 to 15% by weight of the benzotriazole silicone filtering polymer.

13. Process according to claim 10, wherein the composition contains 0.5 to 15% by weight of the benzotriazole silicone filtering polymer.

* * * * *

UNITED STATES PATENT AND TRADEMARK OFFICE
CERTIFICATE OF CORRECTION

PATENT NO.  : 5,618,520
DATED       : April 8, 1997
INVENTOR(S) : Isabelle HANSENNE et al It is certified that error appears in the above-identified patent and that said Letters Patent is hereby corrected as shown below:

Column 12, lines 21-22
   Claim 10, lines 18-19, "containing from" should read -- to --.

Signed and Sealed this

Third Day of March, 1998

Attest:

BRUCE LEHMAN

Attesting Officer

Commissioner of Patents and Trademarks